United States Patent [19]

Johnson et al.

[11] Patent Number: 4,964,411
[45] Date of Patent: Oct. 23, 1990

[54] EVOKED EMG SIGNAL PROCESSING

[75] Inventors: Michael T. Johnson; Alexander Kipnis, both of Minneapolis, Minn.

[73] Assignee: Empi, Inc., St. Paul, Minn.

[21] Appl. No.: 379,415

[22] Filed: Jul. 13, 1989

[51] Int. Cl.$^5$ ............................................. A61B 5/04
[52] U.S. Cl. ................................................... 128/733
[58] Field of Search ................... 128/733, 905; 623/25; 364/413.02, 413.05, 413.27

[56] References Cited

U.S. PATENT DOCUMENTS

| 3,774,593 | 11/1973 | Hakata et al. | 128/733 |
| 4,092,981 | 6/1978 | Ertl | 364/413.05 |
| 4,314,379 | 2/1982 | Tanie et al. | 623/25 |

OTHER PUBLICATIONS

*Motor Responses to Sudden Limb Displacements in Primates with Specific CNS Lesions and in Human Patients with Motor Systems Disorders*, by R. G. Lee and W. G. Tatton, Aug., 1975, p. 285–293, "Le Journal Canadian des Sciences Neurologiques".

*Physiological Mechanisms of Rigidity in Parkinson's Disease*, by A. Berardelli, A. F. Sabra, M. Hallett, "Journal of Neurology, Neurosurgery, and Pachman", p. 45–53.

*Myoelectric Responses at Flexors and Extensors of Human Wrist to Step Torque Perturbations*, by Robert J. Jaeger, Gerald L. Gottlieb and Gyan G. Agarwal, "Journal of Neurophsiology", pp. 388–402, vol. 48, No. 2, Aug., 1982.

*The Fifth Symposium of Motor Control*, by D'Alessio, pp. 625–642.

*Physiology and Mathematics of Myoelectric Signals*, by Carlo de Luca, "Transactions on Biological Engineering", vol. BML-20, No. 6, Jun., 1979.

*Signal Processing for Proportional Myoelectric Control*, by Harry B. Evans, Zushan Pan, Philip A. Parker, and Robert N. Scott, "Transactions on Biological Engineering", vol. BME-31, No. 2, Feb., 1984.

*Some Theoretic Results on a Digital EMG Signal Processor*, by Gian Carlo Filligoi and Paolo Mandarini, "Transactions on Biological Engineering", vol. BME-31, No. 4, Apr., 1984.

*A Nonstationary Model for the Electromyogram*, by Edward Shwedyk, R. Balasubramanian and R. N. Scott, "Transactions on Biomedical Engineering".

*A Signal-to-Noise Investigation of Nonlinear Electromyographic Processors*, by John G. Kreifeldt and Sumner Yao.

*Myoelectric Signal Processing: Optimal Estimation Applied to Electromyography–Part I: Derivation of the Optimal Myoprocessor*, by Neville Hogan and Robert W. Mann.

*Myoelectric Signal Processing: Optimal Estimation Applied to Electromyography–Part II: Experimental Demonstration of Optimal Myoprocessor Performance*, by Neville Hogan and Robert W. Mann.

*A Note on the Time Constant in Low-Pass Filtering of Rectified Surface EMG*, by Hisao Miyano, Tadashi Masuda and Tsugutake Sadoyama, "Transactions on Biomedical Engineering", vol. BME-27, No. 5, May, 1980.

Primary Examiner—Lee S. Cohen
Assistant Examiner—Kevin Pontius
Attorney, Agent, or Firm—Kinney & Lange

[57] ABSTRACT

A method generates signal data which is representative of short and long latency components of myoelectric signals. Production of myoelectric signals is repeatedly evoked in a muscle with triggering events. Myoelectric signal data which is representative of the produced myoelectric signals is stored as a temporal function of the triggering events. The myoelectric signal data is averaged before it is demodulated to produce short latency signal data representative of the short latency components of the myoelectric signals. The myoelectric signal data is also demodulated before it is averaged to produce combined short and long latency signal data. The combined signal data is summed with the short latency signal data to isolate the long latency signal data.

21 Claims, 2 Drawing Sheets

EVOKED EMG SIGNAL PROCESSING

BACKGROUND OF THE INVENTION

1. Field of the Invention

The present invention relates to a method for processing myoelectric signal data. More particularly, the present invention relates to a method for separating signal data representative of spinal and supraspinal signal components of myoelectric signals.

2. Description of the Prior Art

Electromyographic signals (EMG or myoelectric signals) are used to gauge the contraction of muscles during skeletal movements. Muscle tension has been found to be monotonically related to the amplitude of rectified and integrated EMG signals. Much research has been directed towards refining the EMG signals for use as a source of control information for a prosthetic extremity.

There are traditionally two methods of acquiring EMG signals. With the first method, the EMG signals are typically sampled over long time intervals and are not averaged. The EMG signals acquired through this method are referred to as long latency, unaveraged EMG signals. Their signal character is one of an amplitude modulated, random noise carrier signal and is defined by the equation:

$$e(t)=m(t)*n(t) \qquad \text{Eq. 1}$$

where e(t) is the long latency EMG signal as a function of time, m(t) is a modulation function related to muscle contraction and n(t) is a random noise carrier.

Processing of e(t) to provide an estimation of muscle shortening or torque production requires demodulation (i.e., use of a nonlinear element), generally taking the form of rectification and low pass filtering, to produce m(t). The demodulated signal, m(t), can then be averaged over a number of repetitions if an external trigger event is present to increase the signal-to-noise ratio for m(t). If e(t) is not demodulated, and if e(t) is averaged over a sufficient number of repetitions, e(t) approaches a zero level signal. This result is verified by published experimental observation.

With the second method, EMG signals are acquired from a muscle subjected to a rapid stretch or from a muscle subjected to any other means of activating the stretch reflex (e.g., electrical stimulation). The EMG signals acquired through use of the second method are used to assess the function of spinal and supraspinal (cortically-based) reflex. With the second method, the EMG signals are sampled over a short duration, usually less than one second, and are averaged over many repetitions triggered by the onset of a mechanical or electrical trigger. The EMG signals acquired through the second method are referred to as short latency, averaged EMG signals.

Traditionally, the signal processing of short latency, averaged EMG signals has taken the same form as the signal processing for long latency, unaveraged EMG signals (e.g., demodulation by rectification and low pass filtering before averaging). Implicit in using this processing scheme is the acceptance of equation (1) as an accurate mathematical representation of the short latency, averaged EMG signals. In other words, using demodulation before averaging in the signal processing scheme for short latency EMG signals reflects the traditional thinking that failure to demodulate before averaging will result in a zero level signal after averaging a sufficient number of cycles.

SUMMARY OF THE INVENTION

In contrast to the previous public domain teaching, it has been discovered that short latency, averaged EMG signals do not conform to the amplitude modulated, random noise carrier model represented by equation (1). Rather, a non-zero signal results from averaging a large number of repetitions of short latency EMG signals before they are demodulated (e.g., before they are rectified and filtered). If the short latency EMG signals actually did conform to the mathematical representation indicated by equation (1) and if they were averaged without demodulation, a zero level signal would result. Therefore, experimental results reveal a mathematical representation of the short latency EMG signals as given by the following equation:

$$e(t)=m(t)*n(t)+a(t) \qquad \text{Eq. 2}$$

where e(t), m(t) and n(t) of equation (1) are modified by the addition of a(t). In equation (2), a(t) describes an averaged, cycle-locked function which is related to a potential in the muscle that is evoked by synchronous activation of the muscle. It is speculated that this evoked potential is attributable to a population of motor endplate potentials evoked by the synchronous muscle activation. However, it is known that the evoked potential is synchronous with, or has an accurate temporal relationship to the muscle activation. Also, it is known that when e(t) in equation (2) is averaged without demodulation, the a(t) term remains representing the short latency EMG signals.

The present invention is a method for separating signal components of EMG signals into short latency and long latency, or spinal and supraspinal components. The production of myoelectric signals in a muscle is repeatedly evoked with triggering events. The myoelectric signal data, which is representative of the produced myoelectric signals, is stored as a temporal function of the triggering events. The myoelectric signal data is averaged, before being demodulated, to produce short latency signal data representative of the short latency components of the myoelectric signals. The myoelectric signal data is also demodulated, then averaged to produce combined short and long latency signal data. The long latency signal data is then isolated as the difference between the combined and the short latency signal data.

An isolated short latency (or short epoch) EMG signal component of the EMG signals (represented by a(t)) is capable of being used in many forms of diagnostics. Some uses include diagnostics for motor endplate disease, multiple sclerosis (and other diseases resulting from inordinate dispersion of nerve impulses) and spinal dysfunction indicated by spinal synaptic delays. By studying an isolated short latency EMG signal, a physician or other trained specialist could have the ability not only to determine whether a patient is affected with these diseases, but could quantify the degree to which the patient is affected by them.

Similarly, there are many diagnostic and other uses for an isolated long latency (or long epoch) EMG signal component of the EMG signals (represented by m(t)). In essence, the isolated m(t) term represents the amount of time required for the activated muscle to receive supraspinal influences such as cortical or subcortical influences. These long latency EMG signals are useful in the study of cortical dysfunction, the subcortex, and pyramidal tract dysfunction.

DETAILED DESCRIPTION OF THE PREFERRED EMBODIMENTS

Figure 1:
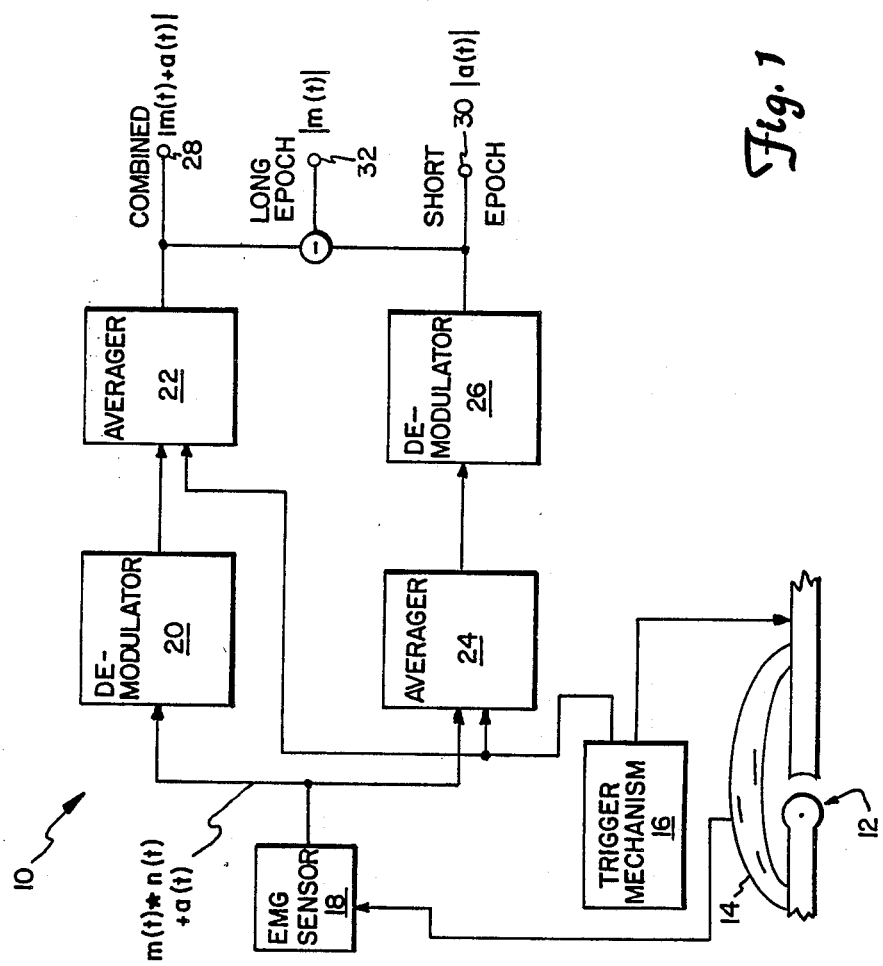
FIG. 1 is a block diagram of the signal processing system of the present invention.

FIG. 1 is a block diagram of signal processing system 10 of the present invention. A portion of two bones are shown which comprise joint 12. Muscle 14 is attached to the bones across joint 12. Signal processing system 10 includes trigger mechanism 16, EMG sensor 18, demodulator 20, averager 22, averager 24 and demodulator 26. Electromyographic signals (EMG signals) are evoked in muscle 14 by a triggering event provided by trigger mechanism 16. The triggering event evokes the EMG signals by activating a muscle spindle receptor mediated stretch reflex in muscle 14. This can be done by a variety of methods such as by producing a torque on one of the bones comprising joint 12 to stretch muscle 14, or by artificially activating a fiber from a muscle spindle receptor in muscle 14 (e.g., electrically stimulating a mixed motor-sensory nerve).

The EMG signals which are evoked in muscle 14 by the triggering event are sensed by EMG sensor 18. EMG sensor 18 is typically a set of gross electrodes which are cutaneous, percutaneous or implanted. EMG sensor 18 senses both short and long latency components of the EMG signals.

Long latency components of the EMG signals (sometimes referred to simply as long latency EMG signals) are signals sensed in muscle 14 which occur more than 100–200 milliseconds after the triggering event. Long latency EMG signals are also referred to as cortically originated, volitional, dispersive, latent or supraspinal originated EMG signals. They are represented by the function :

$$e(t) = m(t) * n(t) \qquad \text{Eq. 1}$$

where m(t) is derived by demodulating e(t) and where n(t) is a random noise carrier. Long latency EMG signals characterized by equation (1) approach a zero signal level when averaged over a sufficient number of repetitions before being demodulated.

Short latency components of the EMG signals (sometimes referred to simply as short latency EMG signals) are those signals which are sensed in muscle 14 during the first 100–200 milliseconds after the triggering event occurs. Short latency EMG signals are also referred to as spinal originated, reflex originated or synchronous EMG signals. Short latency EMG signals are represented by equation (2) which is developed by adding the term a(t) to equation (1). Short latency EMG signals characterized by equation (2) do not approach a zero signal level when averaged before being demodulated.

EMG sensor 18 generates a signal which is representative of the EMG signals evoked in muscle 14. This signal is provided to demodulator 20 where it is demodulated. Demodulation can take one of any known forms. In one embodiment, the signal provided by EMG sensor 18 is demodulated by rectifying and low pass filtering the signal. The demodulated signal is then provided to signal averager 22 where it is event-trigger averaged with a number of other demodulated signals which were evoked by, and acquired after triggering events. The event-triggered averaging can be accomplished by using a digital computer with memory (not shown) for storing signal representations and computing a running average, or by using other known signal averaging techniques. The event-triggered averaging improves the signal-to-noise ratio of the demodulated signal.

The signals appearing at combined output 28 of averager 22 were demodulated before being averaged. Therefore, the signals appearing at combined output node 28 consist of signals represented by both the m(t) and a(t) terms. Hence, both the short latency and long latency components of the EMG signals sensed in muscle 14 are provided at combined output 28. These signals are referred to as combined EMG signals.

The signal generated by EMG sensor 18 is also provided to averager 24. As with averager 22, event-triggered averaging takes place in averager 24. However, in this case, the event-triggered signal provided by EMG sensor 18 is synchronously averaged with other event-triggered signals before it is demodulated. Since the signal provided from EMG sensor 18 is averaged before demodulation, the amplitude modulated, random noise carrier signal m(t)*n(t) becomes zero when averaged over a sufficient number of repetitions. Therefore, the short latency component of the EMG signals mathematically represented by the term a(t) is isolated.

In this embodiment, the isolated short latency signal component provided by averager 24 is demodulated by demodulator 26. Although demodulator 26 is optional, demodulating the short latency signal component provided by averager 24 allows direct comparison of the short latency signal component of the EMG signals with the combined EMG signals appearing at combined signal output 28 of averager 22. By subtracting (at summing junction 29) the short latency signal component appearing at short latency output 30 from the combined EMG signals appearing at combined output 28, the long latency component of the EMG signals is isolated and provided at long latency output 32.

The EMG signals sensed by EMG sensor 18 are temporally synchronized to facilitate accurate averaging. To accomplish temporal synchronization, each cycle of averaging in both averager 22 and averager 24 is coordinated with the triggering event. In the embodiment shown, averagers 22 and 24 are coupled to trigger mechanism 16 for this purpose.

Figure 2:
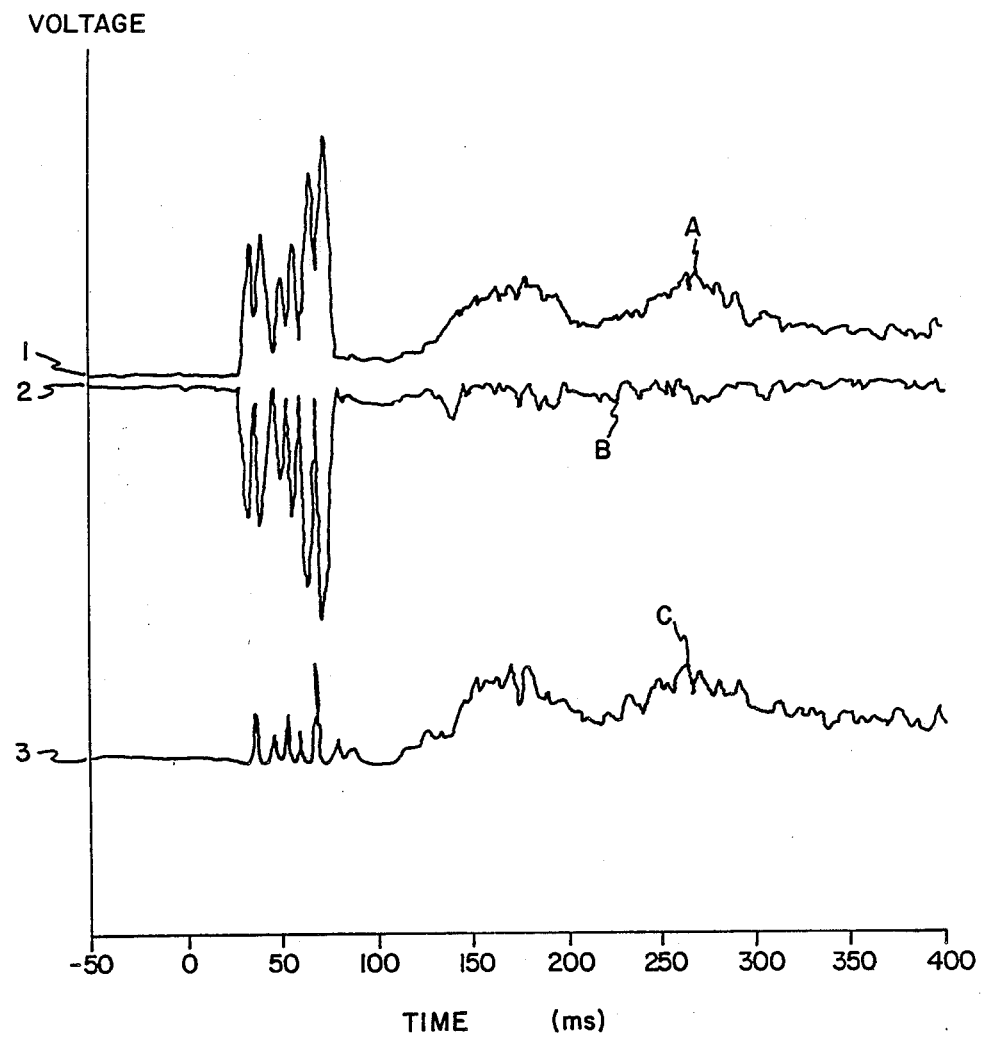
FIG. 2 shows traces representing signals processed by the signal processing system of the present invention.

FIG. 2 shows signal traces A, B and C representing experimental signals processed by signal processing system 10. The traces are graphed on a graph with time along the x axis and voltage along the y axis. The time axis begins at a point 50 ms before the occurrence of a triggering event.

Trace A is a representation of the combined short and long latency signal components of the evoked EMG signals as they appear at combined output 28. Trace B is an inverted representation of the short latency signal component of the evoked EMG signals as they appear at short latency output 30. Trace C is a representation of the long latency signal components of the evoked EMG signals as they appear at long latency output 32.

Traces A, B and C have all been plotted on the same graph and separated for simplicity of comparison. Therefore, the voltage axis should not be read as continuous and each trace should be assumed to start at approximately the same voltage level (i.e., points 1, 2 and 3 all represent approximately the same voltage level). The EMG signals represented by traces A, B and C were evoked in the flexor capri ulnaris by a triggering event comprising a torque step of 0.75 Nm being applied to extend the wrist joint. Also, traces A, B and C represent the average of EMG signals evoked by 150 repetitions of the triggering event.

It should be noted that subtraction of the short latency signal components at short latency output 30 (trace B) from the combined signal at combined output 28 (trace A) results in the long latency signal components appearing at long latency output 32 (trace C). Trace C has a signal level which is nearly zero for the first 100 milliseconds after the triggering event. This signifies an almost exclusive predominance of the short latency signal components (represented by the a(t) term) in the initial 100 milliseconds. After 100 milliseconds, a divergence becomes apparent. Trace A remains at a significant level even after subtraction of trace B. Statistically, this activity is shown to be attributed to a more complex, cortical input to muscle 14.

Signal processing system 10 not only separates the short and long latency components of the signal sensed by EMG sensor 18, but also provides event arrival times. The event arrival times are seen in FIG. 2 as the time between the triggering event and the significant voltage peaks in traces A, B and C. These arrival times appear to correspond to the time between the synchronous muscle activation (i.e., the triggering event) and a population of motor endplate potentials evoked by the synchronous muscle activation.

It should be noted that, although the above discussion was presented with reference to stretching muscle 14 in order to evoke myoelectric signals in muscle 14, the myoelectric signals may also be obtained by an electrical stimulation and recording technique which includes electrically stimulating a mixed (motor and sensory) nerve attached to muscle 14 over which EMG sensing electrodes are attached. This can be accomplished using stimulating electrodes that emit a stimulating electrical signal and that, as with the sensing electrodes, can be cutaneous, percutaneous or implanted. The electrical signal activates reflex mediated synchronous alpha motorneuron inputs to muscle 14 which are capable of being sensed by the same electrode configuration previously described for EMG sensor 18.

This electrical stimulation and recording technique is well know as the Hoffman reflex (H-reflex). The Hoffman reflex consists of (1) the electrical activation of a muscle spindle (Ia) afferents, (2) reflex activation via Ia input of the alpha motorneuron and (3) synchronous population input to the muscle fibers and a resultant activation which provides a "primitive" of the signal expected from a synchronous activation of muscle 14. This "primitive" is then used as a template and compared to the reflex-mediated short latency EMG signals acquired from later triggering events. By matching the "primitive" signal and the acquired EMG signals, through known cross-correlation techniques, a point can be determined which marks a time delay after a triggering event where there is a high probability for synchronous population activation of the muscle.

The present invention is a method for generating data representative of short latency, long latency and combined short and long latency signal components of EMG signals. The EMG signals are evoked by activating the muscle spindle receptor mediated stretch reflex. This is accomplished by stretching the muscle or electrically stimulating a mixed motor-sensory nerve (i.e., artificially activating the fibers from the muscle spindle receptors).

An EMG response occurs in muscle 14 approximately 20 to 60 milliseconds (but generally within 100 ms) after the activation. This reflects the time for activation of muscle spindle stretch receptors, transmission of an impulse to the spinal cord via afferent nerve fibers, synaptic delays due to spinal and supraspinal processing and transmission time of an impulse to muscle 14 via alpha motorneurons. The EMG signals occurring in approximately the first 100 milliseconds after the triggering event are attributed to spinal reflexes. After that, cortical influences, delayed by longer transport routes and complex processing, contribute to the EMG signals.

The sensed EMG signals are subjected to two signal processing sequences one of which is designed to produce a combined signal comprising both the short and long latency components of the EMG signals. The second is designed to isolate the short latency components of the EMG signals. By subtracting the short latency components of the EMG signals from the combined components, the long latency components of the EMG signals are isolated.

The short latency signal components of the EMG signals are useful in the study of motor endplate disease, any diseases which result from dispersion of nerve impulses such as multiple sclerosis and spinal dysfunction resulting from spinal synaptic delays. Typically, these diseases can be studied by examining the latency and dispersion of the short latency signals as well as the peak amplitude. The long latency signals are useful in the study of cortical dysfunction (such as Alzheimer's and acute insults such as strokes), in studying the subcortex (the cerebellum and basal ganglia) and in studying pyramidal tract dysfunction. Therefore, separation of the short and long latency signals is very useful.

Although the present invention has been described with reference to preferred embodiments, workers skilled in the art will recognize that changes may be made in form and detail without departing from the spirit and scope of the invention.

What is claimed is:

1. A method of separating dispersive and synchronous time varying myoelectric signals, comprising:
   repeatedly evoking the production of myoelectric signals in a muscle with triggering events;
   storing myoelectric signal data representative of the produced myoelectric signals as temporal functions of the triggering events;
   averaging the myoelectric signal data before any demodulation of the data to produce short latency signal data representative of the short latency components of the myoelectric signals;
   demodulating the short latency signal data to obtain demodulated short latency signal data;
   demodulating the myoelectric signal data before averaging;
   averaging the demodulated myoelectric signal data to obtain combined data representative of short and long latency myoelectric signals; and
   combining the combined data with the demodulated short latency signal data to isolate long latency signal data representative of long latency components of the myoelectric signals.

2. The method of claim 1 wherein the step of demodulating the short latency signal data further comprises:

rectifying the short latency signal data; and
filtering the short latency signal data.

3. The method of claim 1 wherein the step of demodulating the myoelectric signal data further comprises:
rectifying the signal data; and
filtering the signal data.

4. The method of claim 1 wherein the step of repeatedly evoking production of myoelectric signals further comprises:
activating a muscle spindle receptor mediated stretch reflex.

5. The method of claim 4 wherein the step of activating further comprises:
stretching the muscle.

6. The method of claim 1 wherein the step of repeatedly evoking production of myoelectric signals further comprises:
artificially activating fibers from muscle spindle receptors.

7. The method of claim 6 wherein the step of artificially activating fibers further comprises:
electrically stimulating a mixed motor-sensory nerve.

8. The method of claim 1 wherein the step of storing myoelectric signal data further comprises:
storing activation data representative of activation of muscle fibers in the muscle caused by signals provided to the muscle by alpha motorneurons in response to the triggering event.

9. A method for generating signal data representative of short latency, long latency and combined short and long latency signal components of myoelectric signals, comprising:
repeatedly evoking the production of myoelectric signals in a muscle with triggering events;
storing myoelectric signal data representative of the myoelectric signals produced in the muscle as temporal functions of the triggering events;
averaging the myoelectric signal data, before demodulating the myoelectric signal data, to produce short latency signal data representative of the short latency signal components of the myoelectric signals;
demodulating the myoelectric signal data, before averaging the myoelectric signal data, to produce demodulated signal data;
averaging the demodulated signal data to produce combined signal data representative of the short and long latency signal components of the myoelectric signals; and
combining the short latency signal data with the combined signal data to produce long latency signal data representative of the long latency signal components of the myoelectric signals.

10. The method of claim 9 and further comprising:
demodulating the short latency signal data, before the step of combining, to produce demodulated short latency signal data.

11. The method of claim 10 wherein the step of demodulating further comprises:
rectifying the short latency signal data; and
filtering the short latency signal data.

12. The method of claim 9 wherein the step of demodulating further comprises:
rectifying the myoelectric signal data; and
filtering the myoelectric signal data.

13. A method for separating signal data representing short latency signal components of myoelectric signals from signal data representing long latency and short latency signal components of the myoelectric signals, comprising:
triggering the production of myoelectric signals in a muscle a plurality of times with triggering events;
storing myoelectric signal data, representative of the myoelectric signals, as temporal functions of the triggering events;
averaging the myoelectric signal data before demodulating the data to produce short latency signal data representative of the short latency signal components of the myoelectric signals;
demodulating the short latency signal data;
demodulating the myoelectric signal data stored to produce demodulated myoelectric signal data;
averaging the demodulated myoelectric signal data to obtain combined signal data representative of short and long latency myoelectric signals; and
combining the short latency signal data with the combined signal data to obtain dispersive signal data representative of the long latency myoelectric signals.

14. The method of claim 13 wherein the step of demodulating the short latency signal data further comprises:
rectifying the short latency signal data; and
filtering the short latency signal data.

15. The method of claim 13 wherein the step of demodulating the myoelectric signal data further comprises:
rectifying the myoelectric signal data; and
filtering the myoelectric signal data.

16. A method of separating a plurality of signal components of myoelectric signals comprising:
triggering, with a triggering event, myoelectric signals in a muscle;
storing signal data representative of the myoelectric signals as a temporal function of the triggering event;
repeating the steps of triggering and storing a plurality of times;
averaging the signal data stored, before demodulating, to increase signal to noise ratio and to substantially eliminate components of the signal data representative of cortically generated myoelectric signals;
demodulating the signal data which was averaged;
demodulating the signal data stored, before averaging to produce demodulated signal data;
averaging the demodulated signal data to obtain combined signal data representative of short and long latency myoelectric signals; and
combining the short latency signal data with the combined signal data to produce dispersive data representative of long latency myoelectric signals.

17. The method of claim 16 wherein the step of demodulating the signal data which was averaged further comprises:
rectifying the signal data which was averaged; and
filtering the signal data which was rectified.

18. The method of claim 16 wherein the step of demodulating the signal data stored further comprises:
rectifying the signal data; and
filtering the signal data.

19. A method of separating supraspinal originated electromyographic (EMG) signals from spinal originated EMG signals comprising:
applying a triggering input to a muscle to induce EMG signals in the muscle;

synchronizing detection of the EMG signals with the triggering input;

storing data representative of the signals being detected as a time function of the triggering input;

repeating the steps of applying, synchronizing and storing a plurality of times;

averaging the data representative of the EMG signals which was stored, before demodulating, to produce an averaged signal representation representative of the spinal originated EMG signals;

demodulating the averaged signal representation to obtain a demodulated averaged signal representation;

demodulating the data stored to obtain demodulated data;

averaging the demodulated data to obtain combined signal data representative of spinal and supraspinal originated EMG signals; and combining the demodulated averaged signal representation with the combined signal data to produce dispersive data representative of the supraspinal originated EMG signals.

20. The method of claim 19 wherein the step of demodulating the averaged signal representation further comprises:

rectifying the averaged signal representation; and filtering the averaged signal representation to produce an averaged, rectified signal representation.

21. The method of claim 19 wherein the step of demodulating the data stored further comprises:

rectifying the data stored; and filtering the data stored.